US008981146B2

(12) United States Patent
Tolan et al.

(10) Patent No.: US 8,981,146 B2
(45) Date of Patent: Mar. 17, 2015

(54) RECOVERY OF VOLATILE CARBOXYLIC ACIDS BY A STRIPPER-EXTRACTOR SYSTEM

(75) Inventors: Jeffrey S. Tolan, Ontario (CA); Brian Foody, Ontario (CA); Vijay Anand, Ontario (CA)

(73) Assignee: Iogen Energy Corporation, Ontario (CA)

( * ) Notice: Subject to any disclaimer, the term of this patent is extended or adjusted under 35 U.S.C. 154(b) by 429 days.

(21) Appl. No.: 13/392,744

(22) PCT Filed: Aug. 18, 2010

(86) PCT No.: PCT/CA2010/001272
§ 371 (c)(1),
(2), (4) Date: May 7, 2012

(87) PCT Pub. No.: WO2011/022811
PCT Pub. Date: Mar. 3, 2011

(65) Prior Publication Data
US 2012/0209028 A1    Aug. 16, 2012

Related U.S. Application Data

(60) Provisional application No. 61/237,397, filed on Aug. 27, 2009.

(51) Int. Cl.
*C07C 51/44*     (2006.01)
*B01D 3/38*      (2006.01)
*C12F 3/00*      (2006.01)

(52) U.S. Cl.
CPC ............... *C12F 3/00* (2013.01); *C07C 51/445* (2013.01); *Y02E 50/16* (2013.01)
USPC .......................................... 562/512; 562/608

(58) Field of Classification Search
USPC ................................................. 562/512, 608
See application file for complete search history.

(56) References Cited

U.S. PATENT DOCUMENTS 114,517 A    5/1871   Bell
118,788 A    9/1871   Burcey
(Continued)

FOREIGN PATENT DOCUMENTS

CN    1944374 A      4/2007
CN    101306989 B    4/2011
(Continued)

OTHER PUBLICATIONS

Adams and Voorhees, Organic Syntheses, Coll. vol. p. 280 (1941); or vol. 1, p. 49 (1921).*
(Continued)

*Primary Examiner* — Brandon Fetterolf
*Assistant Examiner* — Janet L Coppins
(74) *Attorney, Agent, or Firm* — Fitzpatrick, Cella, Harper & Scinto

(57) ABSTRACT

A process for recovering a volatile carboxylic acid from an aqueous stream comprising same, the process comprising the steps of: (i) steam stripping the carboxylic acid from the aqueous stream, which aqueous stream is produced by a conversion process using a lignocellulosic feedstock as a substrate, the steam stripping comprising contacting the aqueous stream with steam by flowing the aqueous stream and the steam countercurrent to one another, thereby producing a vapor stream comprising vaporized carboxylic acid and steam and a stripped aqueous stream; (ii) extracting the vaporized carboxylic acid with an organic solvent by contacting the vapor stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water; (iii) returning the steam from step (ii) to the steam stripping step (step i) to further strip the carboxylic acid from the aqueous stream; and (iv) separating the carboxylic acid from the organic solvent.

16 Claims, 2 Drawing Sheets

TWO STAGE STRIPPER/EXTRACTOR FOR ACETIC ACID RECOVERY

(56) References Cited

U.S. PATENT DOCUMENTS

| | | | |
|---|---|---|---|
| 939,980 | A | 11/1909 | Chute |
| 998,234 | A | 7/1911 | Crossley et al. |
| 1,052,446 | A | 2/1913 | Volney |
| 1,192,987 | A | 8/1916 | Campbell |
| 1,314,765 | A | 9/1919 | Stone |
| 1,858,150 | A | 5/1932 | Gorhan |
| 1,993,259 | A | 3/1935 | Buc |
| 2,266,718 | A | 12/1941 | Bludworth |
| 2,444,527 | A | 7/1948 | Pomeroy |
| 2,471,942 | A | 5/1949 | Drew |
| 3,084,109 | A | 4/1963 | Ure et al. |
| 3,177,263 | A | 4/1965 | Francis |
| 3,490,997 | A | 1/1970 | Burney et al. |
| 3,530,043 | A | 9/1970 | Horn |
| 3,530,044 | A | 9/1970 | Horn |
| 3,951,755 | A | 4/1976 | Sartorius et al. |
| 4,088,660 | A | 5/1978 | Puurunen |
| 4,100,189 | A | 7/1978 | Mercier |
| 4,102,705 | A | 7/1978 | Pfeiffer et al. |
| 4,342,831 | A | 8/1982 | Faber et al. |
| 4,353,784 | A | 10/1982 | Koga et al. |
| 4,396,463 | A | 8/1983 | Josis et al. |
| 4,401,514 | A | 8/1983 | Kanzler et al. |
| 4,898,644 | A * | 2/1990 | Van Horn .................. 203/15 |
| 4,978,430 | A | 12/1990 | Nakagawa et al. |
| 5,162,214 | A | 11/1992 | Hubred |
| 5,175,357 | A | 12/1992 | Van Brunt |
| 5,264,623 | A | 11/1993 | Oehr et al. |
| 5,306,398 | A | 4/1994 | Seidel et al. |
| 5,399,751 | A | 3/1995 | Gentry et al. |
| 5,492,603 | A | 2/1996 | Gualy et al. |
| 6,662,780 | B2 | 12/2003 | Yook |
| 6,793,777 | B1 | 9/2004 | Rudinger et al. |
| 6,955,743 | B2 | 10/2005 | Rousu et al. |
| 7,048,835 | B2 | 5/2006 | Jang et al. |
| 7,196,218 | B2 | 3/2007 | Gaddy et al. |
| 2007/0068792 | A1 | 3/2007 | Jang et al. |

FOREIGN PATENT DOCUMENTS

| | | |
|---|---|---|
| EP | 1520847 | 4/2005 |
| GB | 774809 | 5/1957 |
| GB | 1407523 | 9/1975 |
| WO | 02/053829 | 7/2002 |
| WO | 03/074781 | 9/2003 |

OTHER PUBLICATIONS

E.L. Heric et al, Distribution of Acetic and Propionic Acids Between Furfural and Water, Journal of Chemical and Engineering Data, vol. 5, No. 3 (1960) 272-74.

E.L. Heric et al., Distribution of Burytic Acid between Furfural and Water at 25 degrees and 35 degrees celcius, Journal of Chemical and Engineering Data, vol. 11, No. 1 (1966) 38-40.

B. Schierbaum et al., Isolation of Carboxylic Acids from Aqueous Solutions by Extraction with Dialkylcarboxylic Amides/Trialkylamines, Chem. Eng. Tech., vol. 22 (1999) 37-41.

N.L. Ricker et al., Solvent Extraction with Amines for Recovery of Acetic Acid from Dilute Acqueous Industrial Streams, J. Separ. Proc. Technol. vol. 1, No. 2 (1980) 23-30.

K.J. Zeitsch, The Chemistry and Technology of Furfural and its Many By-Products, ACS Sugar Series, vol. 13, (2000) 111-13.

L. Lei et al., Separation of acetic acid and water by complex extractive distillation, Separation and Purification Technology, vol. 36 (2004) 131-38.

* cited by examiner

US 8,981,146 B2

RECOVERY OF VOLATILE CARBOXYLIC ACIDS BY A STRIPPER-EXTRACTOR SYSTEM

This application is a national stage application of PCT/CA2010/001272 having an international filing date of Aug. 18, 2010, which claims benefit of U.S. provisional application No. 61/237,397 filed Aug. 27, 2009, both of which are incorporated by reference herein.

FIELD OF THE INVENTION

The present invention relates to a process for recovering carboxylic acids, more particularly volatile carboxylic acids from an aqueous stream.

BACKGROUND OF THE INVENTION

Carboxylic acids are valuable chemicals that are employed in many applications in industry. For example, acetic acid has a wide ranByge of uses, including in the chemical industry to produce cellulose acetate, rayon acetate, acetic anhydride and plastics and in the food industry as a preservative. Acetic acid is produced both synthetically and by bacterial fermentation. Most of the acetic acid produced for the chemical industry is made by methanol carbonylation, whereby methanol and carbon monoxide are reacted to produce acetic acid. Acetic acid that is used as a food additive is produced by the biological route, as many nations' food purity laws stipulate that vinegar used in foods must be of biological origin. Other carboxylic acids of industrial importance include formic acid and propionic acid. Formic acid can react to form esters and is used as a preservative in animal feeds while propionic acid is the flavorant in Swiss cheese.

Recovering acetic acid that is produced as a byproduct from lignocellulosic conversion processes has received much attention in recent years. Agricultural wastes are of particular interest as they are inexpensive, and are often burned or landfilled. There is an enormous untapped potential for their use not only as a source of fermentable sugar to produce fuels such as ethanol or butanol, but also as a source of byproducts, such as acetic acid In the production of fermentable sugar from lignocellulosic feedstocks, the acetic acid arises from the hydrolysis of acetyl groups present on the hemicellulose and lignin components of the feedstock. For instance, the acetic acid may originate from an acid pretreatment, which is conducted to hydrolyze the hemicellulose component of the feedstock, but with limited hydrolysis of the cellulose. The cellulose is then hydrolyzed with cellulase enzymes and the glucose so produced is fermented to ethanol, butanol or other fermentation products. Other known methods for producing sugar hydrolyzate streams that also contain acetic acid or acetate salts include alkali pretreatment conducted under conditions that result in hemicellulose hydrolysis, followed by enzymatic hydrolysis of cellulose with cellulase enzymes or complete acid hydrolysis conducted in a single step under harsher conditions so that both the hemicellulose and cellulose present in the feedstock are hydrolyzed. Acetic acid can also be produced as a byproduct in other industries that utilize lignocellulosic materials as feedstocks, including during furfural production and in the pulp and paper industry.

Formic acid is also a byproduct produced during the pretreatment of lignocellulosic feedstocks, specifically by sugar and lignin degradation that occurs during such processes. Formic acid is also produced as a byproduct during furfural production from lignocellulosic feedstocks, along with acetic acid.

Whether or not the recovery of carboxylic acids from industrial process streams is feasible depends on the cost of the recovery, the ability to remove impurities and the ability to concentrate it to a sufficiently high concentration (e.g., in the case of acetic acid as glacial acetic acid). Streams derived from lignocellulosic feedstocks pose particular problems for successful recovery of carboxylic acids due to their multi-component nature and because the concentration of carboxylic acids in such streams is typically low.

Liquid-liquid extraction is a known technique for recovering carboxylic acids. This method, also known as solvent extraction, extracts carboxylic acids with a solvent or mixture of solvents to produce an extract containing the acid and the extracting solvent and typically some of the water in the process stream. The extract may be distilled to recover the extracting solvent for reuse in the process and to obtain a concentrated acid solution free of the solvent. Such extractions may involve the use of organic bases such as alkylamines and phosphine oxides. (See for example Ricker, N. L., Pittman, E. F., and King, C. J., J. Separ. Proc. Technol., 1980, 1(2):23-30).

However, the recovery of carboxylic acids by liquid-liquid extraction at the low concentrations found in process streams resulting from lignocellulosic conversion process, e.g., less than about 2% (w/w), requires significant amounts of the organic solvent in order for the extraction to be effective. This is a major disadvantage as such solvents are costly. Moreover, the solvent often has a high affinity for lignin and other high molecular weight compounds that are present in many of the streams produced during the conversion process. These compounds can accumulate in the solvent and render it less effective. Furthermore, the use of agitation to increase the rate of liquid-liquid extraction often leads to the formation of emulsions of droplets of the aqueous phase within the organic phase. The separation of the emulsified phases can be difficult. Accordingly, liquid-liquid extraction is not preferred for directly recovering acetic acid from streams containing these components.

British Patent No. 1,407,523 discloses a method of recovering acetic acid by extractive rectification. According to the method, a crude acid mixture containing acetic acid is fed into the lower half of a first rectification column either in liquid form or the form of a vapour. The extractant, 1,2-dimorpholylethane, is fed as a liquid in the upper third of the column. The sump product of the first column, which consists of an anhydrous mixture of acetic acid and extractant, is fed continuously to the lower half of the second rectification column. Acetic acid, which is free from water and extractant is taken off as distillate, while a product, consisting essentially of the extractant is obtained as a sump product. A similar process is disclosed by U.S. Pat. No. 3,951,755 (Sartorius et al.) using N-methyl acetamide as the extractant for acetic acid. CN101306989 discloses using a thiocyanate, acetate or nitrate salt in combination with an organic solvent for separating water and acetic acid by extractive distillation. Moreover, Lei et al. (Separation and Purification Technology, 2004, 36:131-138) discloses a "complex extractive distillation" for separating acetic acid and water using tributylamine as the separating agent. However, distillation is a very capital intensive process. Because of this, it is generally conceded as not being worthwhile for concentrating dilute aqueous acetic acid having less than about 30 weight percent acetic acid.

Another method of recovering acetic acid from an aqueous stream involves evaporating the acetic acid and water and then condensing the vapours thus formed, followed by extracting the acetic acid from the condensate by liquid-liquid extraction. Such processes are disclosed by U.S. Pat. No. 4,401,514 (Kanzler et al.) and U.S. Pat. No. 4,102,705 (Pfeiffer et al.). However, condensation and cooling of the vapour requires additional equipment and a large amount of energy, which increases the complexity and cost of the process.

The recovery of acetate salts using evaporation has been disclosed. This involves evaporating acetic acid from solution and contacting the vapourized acetic acid produced in the evaporator with alkali, thereby producing an acetate salt. For example, U.S. Pat. No. 1,314,765 discloses recovering acetic acid from the vapours of vegetable extracts undergoing evaporation in multiple evaporation units. The process involves intimately contacting alkali, such as lime, in the form of a spray, with vapours passing from one unit to another, thereby producing the acetate salt.

U.S. Pat. No. 114,517 discloses a process whereby acetate salt of lime is recovered from acetic acid vapours by contacting the vapours with lime that is placed on trays in a cylindrical vessel. Moreover, U.S. Pat. No. 1,052,446 discloses a process of making acetate of lime that involves contacting vapours containing acetic acid with a hot calcium carbonate solution.

Likewise, U.S. Pat. No. 4,898,644 (Van Horn) discloses a process for recovering an acetate salt as a byproduct produced during the production of furfural. The process involves steam stripping organic acids, including acetic and/or formic acid from an aqueous solution containing same, and contacting the vapourized acetic acid with sodium hydroxide to form sodium acetate. Prior to removing the acetic acid, furfural may be removed from the feed stream in a furfural stripper.

However, a disadvantage of the processes of U.S. Pat. Nos. 4,898,644, 1,314,765, 114,517 and 1,052,446 is that a further step of acidification would be necessary to further purify and recover acetic acid from the solution containing the sodium acetate or calcium acetate. Prior to extraction with a solvent, acidification is necessary so that sodium acetate or calcium acetate is in the non-dissociated form, (i.e., so that it is present predominantly as the acetic acid species, rather than the acetate salt species) and this is typically carried out by using sulfuric acid, which is costly and creates sulfate salts that must be processed. Furthermore, this purification step necessitates a separate liquid-liquid extraction to recover the acetic acid. The increased chemical usage by the acidification and the requirements for additional equipment increase the cost and complexity of the process, which in turn has a negative impact on the economics of the process.

As noted previously, it is known to recover acetic acid as a byproduct during the production of furfural. Furfural is produced from the decomposition of xylose that results from the hydrolysis of the hemicellulose component of lignocellulosic feedstocks, such as wood chips. During such production processes, the raw material is fed into a reactor operating at high temperatures by the introduction of steam to produce furfural, as well as the byproducts, methanol, formic acid and acetic acid. Vapour flowing from the reactor contains water, furfural, formic acid and acetic acid and it is known to separate these acids from one another from this vapour stream and subsequently purify them.

For example, U.S. Pat. No. 4,088,660 (Puurunen) discloses such a process for producing furfural and recovering acetic acid as a byproduct. According to this process, the vapour stream produced from the reactor, containing the furfural, methanol, acetic acid and formic acid, is contacted with furfural in a gas washer and, subsequently, in an absorption tower. The furfural, which is recycled from the process, serves to absorb the acetic acid and part of the water from the vapour, thus producing an aqueous solution containing the organic acids and furfural. This aqueous solution is then dehydrated and subjected to distillation in order to separate the volatile organic acids from the furfural.

However, a drawback of the above process of Puurunen (supra) is that the solubility of furfural in water is 8.3% (83 g/L) and the solubility of water in furfural is about 5%, depending on the temperature. These mutual solubilities are too high for furfural to be an effective extractant of acetic acid from water. That is, the loss of furfural in the water phase and the need to remove water from the furfural phase would add significant cost to the operation. In addition, the extraction of acetic acid by furfural is very weak. The concentration of acetic acid in furfural is less than that in water in an acetic acid-furfural-water extraction system at 35° C. (E. L. Heric and R. M. Rutledge, (1960), Journal of Chemical Engineering Data 5(3): 272-274).

Zeitsch (The Chemistry and Technology of Furfural and its Many Byproducts (2000), ACS Sugar Series, Vol. 13, Elsevier, Köln, Germany, p. 111-113) discloses the use of triethylamine vapour to extract acetic acid vapour and purify it from an aqueous solution. Triethylamine has a boiling point of 89° C. However, triethylamine reacts with acetic acid to form a complex with a high boiling point (165° C.), which complex can be separated from water by distillation. The complex can then be split by reacting it with ethanol at elevated temperature in the presence of an ion exchange resin which produces ethyl acetate, from which acetic acid can be produced. However, since the process is complicated and requires many steps it is impractical for use on an industrial scale.

U.S. Pat. No. 4,342,832 discloses a method of removing toxins of fermentation from an acid hydrolyzate derived from lignocellulosic materials by steam stripping, although the recovery of carboxylic acids from the hydrolyzate was not carried out. The steam stripping involves passing the hydrolyzate through a countercurrent extractor to remove steam volatiles. In this technique, steam is introduced at the bottom of the column and the hydrolyzate is introduced at the top and collected in a vessel at the bottom of the column. Steam volatile toxins, including furfural, are removed in the steam which is condensed and collected in a separate vessel. Sufficient calcium oxide is then added to the steam-stripped hydrolyzate to adjust the pH between 10 and 10.5 and degrade 5-hydroxymethylfurfural.

At present, none of the prior art addresses operating an efficient and economical process for recovering volatile carboxylic acids, such as at the low concentrations found in many industrial process streams, including streams obtained from lignocellulosic conversion processes. The development of such a recovery process remains a critical requirement for the utilization of carboxylic acids as byproducts of economic significance.

SUMMARY OF THE INVENTION

The present invention provides a process for recovering a volatile carboxylic acid from an aqueous stream comprising same, the process comprising the steps of:
(i) steam stripping the carboxylic acid from the aqueous stream, which aqueous stream is produced by a conversion process using a lignocellulosic feedstock as a substrate, the steam stripping comprising contacting the aqueous stream with steam by flowing the aqueous stream and the steam countercurrent to one another, thereby producing a vapour stream comprising vapourized carboxylic acid and steam and a stripped aqueous stream;

(ii) extracting the vapourized carboxylic acid with an organic solvent by contacting the vapour stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water;

(iii) returning the steam from step (ii) to the steam stripping step (step i) to further strip the carboxylic acid from the aqueous stream; and (iv) separating the carboxylic acid from the organic solvent.

According to one embodiment of the invention, the steam stripping is conducted in a stripping column and the extracting is conducted in a separate extracting column. Alternatively, the steam stripping and extracting are conducted in a single column comprising alternating and superimposed stripping and extracting stages.

In another embodiment of the invention, the carboxylic acid in said aqueous stream is less than about 5% w/w.

According to another embodiment of the invention, the carboxylic acid is separated from the organic solvent by distillation. Optionally, the organic solvent obtained from the step of separating is reused in the process.

According to a further embodiment of the invention, in the step of extracting, the organic solvent may comprise an aliphatic amine having at least 10 carbon atoms and an alkylphenol having 1 to 40 carbon atoms in its alkyl group. The alkylphenol may be nonylphenol or octylphenol. The aliphatic amine may be selected from the group consisting of tributylamine, tripentylamine, trihexylamine, trioctylamine, tridecylamine and mixtures thereof. In a further embodiment of the invention, water is insoluble in the organic solvent.

The aqueous stream can be produced by a conversion process using a lignocellulosic feedstock as a substrate. The lignocellulosic feedstock may be selected from the group consisting of corn stover, soybean stover, corn cobs, rice straw, rice hulls, switch grass, corn fiber, wheat straw, barley straw, canola straw, oat straw, oat hulls and combinations thereof.

In another embodiment of the invention, the aqueous stream that is stripped is a fermentation broth comprising a fermentation product produced by pretreating the lignocellulosic feedstock with acid or alkali so as to produce a pretreated feedstock composition comprising fiber solids containing cellulose, hydrolyzing the cellulose to glucose and then fermenting the glucose to produce the fermentation broth comprising the fermentation product. Alternatively, the aqueous stream that is stripped may be a still bottoms stream produced by pretreating the lignocellulosic feedstock with acid or alkali so as to produce a pretreated feedstock composition comprising fiber solids containing cellulose, hydrolyzing the cellulose to glucose, fermenting the glucose to produce a fermented solution comprising ethanol and distilling the fermented solution to produce concentrated ethanol and the still bottoms stream.

The aqueous stream that is stripped may also be a stream produced by hydrolyzing hemicellulose and cellulose present in the lignocellulosic feedstock with acid or alkali.

In yet a further embodiment of the invention, the stripping is conducted at a temperature of 40° C. to 145° C., more preferably 60° C. to 120° C. The extracting may be conducted at a temperature of about 60° C. to about 175° C.

Preferably, the carboxylic acid that is recovered is acetic acid.

The foregoing process provides a simplified and cost-effective means to recover volatile carboxylic acids. Advantageously, the process of the invention does not require a subsequent acidification step to recover carboxylic acids, including, but not limited to acetic acid. This is in contrast to prior art methods in which acetic acid vapour is contacted with alkali to produce a solution containing an acetate salt that must be acidified to the non-dissociated form prior to recovery by liquid-liquid extraction. Thus, the present invention avoids the disadvantages inherent in such processes including the high cost of the acidification and the production of sulfate salts that must be further processed.

Furthermore, by steam stripping the carboxylic acid and contacting the vapours with the organic solvent, rather than, for example, evaporating the liquid stream containing the carboxylic acid and then condensing and extracting the acid from the condensate, the use of additional equipment for condensing is avoided, as well as the high energy costs associated with such a step.

The process of the invention also overcomes the disadvantages inherent with the use of furfural to extract acetic acid, namely that furfural has a significant solubility in water. The dissolution of furfural in water is a significant cost in the process and limits the use of the water stream in the plant.

Moreover, the recovery process of the invention can be applied to a wide range of industrial process streams containing carboxylic acids, including those containing lignin and high molecular weight compounds. By contrast, liquid-liquid extraction processes are ineffective when used to recover carboxylic acids directly from streams containing these components as they can accumulate in the solvent and render it less effective.

DETAILED DESCRIPTION OF THE INVENTION

Figure 1:
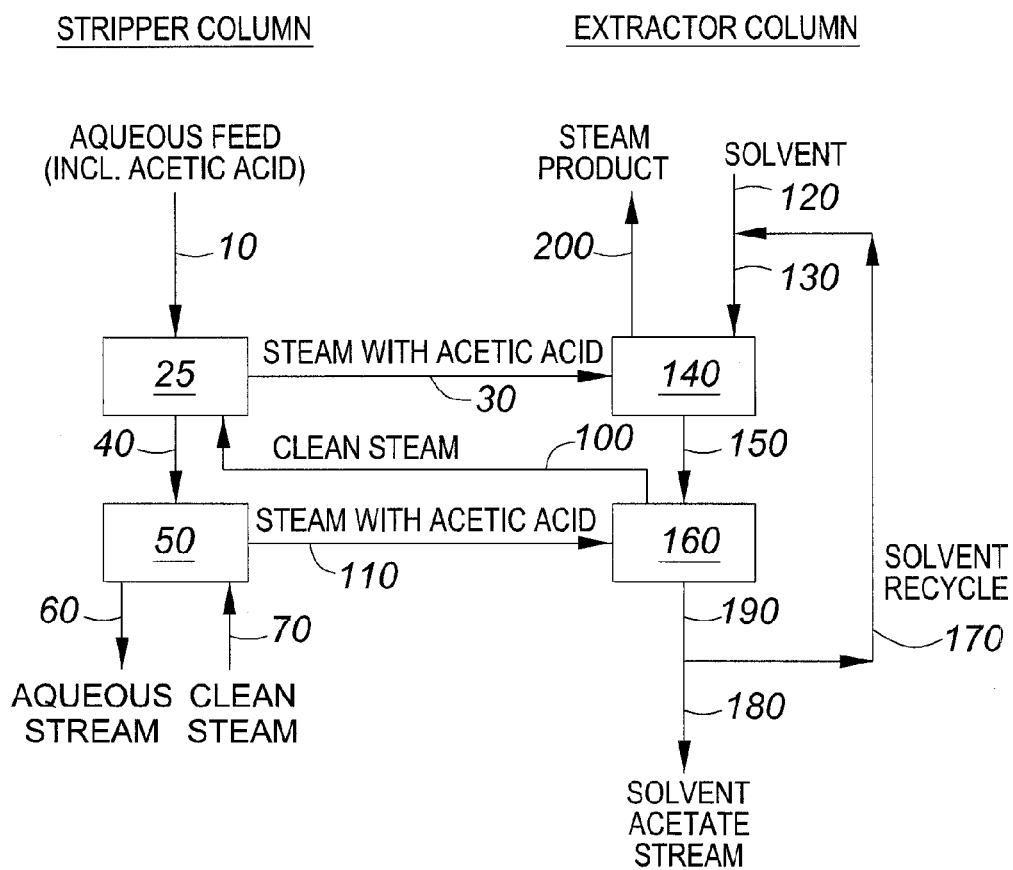
FIG. 1 is a process flow diagram for recovering a volatile carboxylic acid according to an embodiment of the invention.

The following description is of preferred embodiments.

Carboxylic acids are organic acids characterized by the presence of at least one carboxyl group, denoted —COOH. Carboxylic acids may have more than one carboxyl group, but the presence of one carboxyl group is preferred. The simplest and preferred carboxylic groups for use in the present invention are the alkanoic acids, which are carboxylic acids of the form R—COOH. Examples of these are acetic acid, formic acid, and propionic acid. Furthermore, one or more carboxylic acids may be recovered in accordance with the invention.

The carboxylic acid recovered in accordance with the invention is a "volatile carboxylic acid". As used herein, the term "volatile carboxylic acid" refers to a carboxylic acid that has a boiling point at atmospheric pressure of less than 150° C. Compounds with a higher boiling point will not easily be stripped with steam utilized in the practice of the invention. Two examples of compounds that are volatile carboxylic acids are acetic acid (boiling point 118° C.) and formic acid (boiling point 101° C.). The boiling point of the volatile carboxylic acid is preferably at least about 80° C. at atmospheric pressure. Compounds with a boiling point lower than this can be steam stripped without the need of extraction. More preferably, the boiling point of the volatile carboxylic acid is at least about 100° C.

Accordingly, in one embodiment of the invention, the volatile carboxylic acid has a boiling point measured at atmospheric pressure between 80° C. and 150° C., more preferably between 100° C. and 150° C. For example, the boiling point at atmospheric pressure may be 80, 85, 90, 95, 100, 105, 110, 115, 120, 125, 130, 135, 140, 145 or 150° C.

In principal, the process of the invention can be used to recover carboxylic acids from any aqueous stream containing a carboxylic(s) acids derived from an industrial process, regardless of its concentration. However, the process of the invention is particularly advantageous when recovering one or more volatile carboxylic acids from a process stream that contains less than 50 g/L (5%) volatile carboxylic acids.

Thus, in embodiments of the invention, volatile carboxylic acids are present in the aqueous stream at a concentration of between about 0.1 and about 50 g/L, about 0.5 and about 20 g/L or about 1.0 and about 15 g/L. For example, the acetic acid may be present in the sugar stream at a concentration of about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 or 20.0 g/L.

Acetic acid has a $pK_a$ of about 4.75 ($K_a$ of $1.78 \times 10^{-5}$) so that at pH 4.0, about 14.8 mole % of the acid is present as acetate. Accordingly, the species present in the aqueous stream will depend on the pH of the solution. The steam stripping of acetic acid is typically conducted at a pH at which acetic acid is the dominant species in solution, such as pH<pKa, although the aqueous stream may contain some acetate species. Similarly, formic acid has a pKa of 3.75 and is typically steam stripped at a pH below this value.

Although the process of the invention is not constrained by the origin of the aqueous stream comprising volatile carboxylic acids, preferably such stream is derived from a process that uses a lignocellulosic material as a feedstock. According to this embodiment, the acetic acid arises from acetyl groups attached to xylan and to some extent lignin. Acetic acid possibly also arises from other constituents that are liberated as acetic acid and/or acetate by exposure to acid, alkali or other treatments of the feedstock.

Formic acid is a degradation product of sugar produced during pretreatment. Glucose is unstable in hot acid solutions and can lose three molecules of water to yield 5-hydroxymethylfurfural (HMF). HMF in turn is unstable and can add two molecules of water to yield formic acid and levulinic acid.

Representative lignocellulosic feedstocks for use in the practice of the invention are (1) agricultural wastes such as corn stover, corn cobs, wheat straw, barley straw, oat straw, rice straw, canola straw, and soybean stover; (2) grasses such as switch grass, miscanthus, cord grass, and reed canary grass; and (3) forestry wastes such as aspen wood and sawdust. These feedstocks contain high concentrations of cellulose and hemicellulose that are the source of the sugar in the aqueous stream.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch.

The aqueous stream preferably arises from a lignocellulosic conversion process in which a lignocellulosic feedstock is subjected to chemical and/or biological treatment to hydrolyze polysaccharides to produce fermentable sugar, followed by fermentation to produce a fermentation product and optionally a distillation to concentrate the fermentation product. However, streams from pulp processing and furfural production are also encompassed by the present invention as these processes produce streams containing acetic acid and formic acid at low concentrations.

According to one embodiment of the invention, the aqueous stream from which the carboxylic acid is recovered is a stream resulting from pretreating the feedstock with acid, e.g., a hemicellulose hydrolysate. The acid pretreatment is intended to deliver a sufficient combination of mechanical and chemical action so as to disrupt the fiber structure of the lignocellulosic feedstock and increase the surface area of the feedstock to make it accessible or susceptible to cellulase enzymes. Preferably, the acid pretreatment is performed so that nearly complete hydrolysis of the hemicellulose and only a small amount of conversion of cellulose to glucose occurs. The majority of the cellulose is hydrolyzed to glucose in a subsequent step that uses cellulase enzymes, although a small amount of the cellulose can be hydrolyzed in this step as well. Typically a dilute acid, at a concentration from about 0.02% (w/w) to about 5% (w/w), or any amount therebetween, (measured as the percentage weight of pure acid in the total weight of dry feedstock plus aqueous solution) is used for the pretreatment.

Examples of acids that can be used in the pretreatment process include those selected from the group consisting of sulfuric acid, sulfurous acid, sulfur dioxide and a combination thereof. Preferably, the acid is sulfuric acid.

A preferred pretreatment, without intending to be limiting, is steam explosion described in U.S. Pat. No. 4,416,648 (Foody; which is incorporated herein by reference).

The acid pretreatment is preferably carried out at a maximum temperature of about 160° C. to about 280° C. The time that the feedstock is held at this temperature may be about 6 seconds to about 600 seconds. In one embodiment of the invention, the pH of the pretreatment is about 0.4 to about 3.0, or any pH range therebetween. For example, the pH of the pretreatment may be 0.4, 1.0, 1.5, 2.0, 2.5 or 3.0. Preferably, the pretreatment is carried out to minimize the degradation of xylose and the production of furfural.

In another embodiment of the invention, the chemical used for pretreatment of the lignocellulosic feedstock is alkali. The alkali used in the pretreatment reacts with acidic groups present on the hemicellulose to open up the surface of the substrate. With alkali pretreatment, acetate is produced from acetyl groups present on the hemicellulose and/or other components of the feedstock, although the amount of acetate present will vary depending on the severity of the treatment. In contrast to acid pretreatment, alkali pretreatment methods may or may not hydrolyze xylan to produce xylose.

Examples of alkali that may be used in the pretreatment include ammonia, ammonium hydroxide, potassium hydroxide, and sodium hydroxide. The pretreatment may also be conducted with alkali that is insoluble in water, such as lime and magnesium hydroxide, although the soluble bases are preferred.

An example of a suitable alkali pretreatment, that is variously called the Ammonia Freeze Explosion, Ammonia Fiber Explosion or Ammonia Fiber Expansion ("AFEX" process), involves contacting the lignocellulosic feedstock with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat.

Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

The pretreatment produces a pretreated feedstock composition (e.g., pretreated feedstock slurry) that contains a soluble component including the sugars resulting from hydrolysis of the hemicellulose, acetic acid and other organic acids, such as galacturonic acid, formic acid, lactic acid and glucuronic acid and fiber solids including cellulose and lignin.

According to another embodiment of the invention, the soluble component of the pretreated feedstock composition is separated from the solids. This soluble fraction, which includes the sugars released during pretreatment, the acetic acid, formic acid, other organic acids and soluble components may be the aqueous stream fed to the stripper.

The foregoing separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation, using known methods such as centrifugation, microfiltration, plate and frame filtration, cross-flow filtration, pressure filtration, vacuum filtration and the like. Optionally, a washing step may be incorporated into the solids-liquids separation.

The separated solids, which contain cellulose, may then be hydrolyzed to glucose. The hydrolysis may be conducted with cellulase enzymes, which are discussed in more detail hereinafter. The resulting glucose-containing stream may then be the aqueous stream fed to the stripper.

According to yet another embodiment of the invention, the soluble component of the pretreated feedstock composition is not separated from the fiber solids. In this embodiment, the entire pretreated feedstock composition, which will include any sugars resulting from hemicellulose hydrolysis, is subjected to cellulose hydrolysis. This produces a sugar stream that may be the aqueous stream sent to the evaporating step for recovery of carboxylic acids. Preferably, the cellulose hydrolysis is conducted with cellulase enzymes. A major component of this sugar stream will be glucose, although pentose sugars derived from the hemicellulose component will be present as well.

Prior to hydrolysis with cellulase enzymes, the pH of the pretreated feedstock composition is adjusted to a value that is amenable to the cellulase enzymes, which is typically between about 4 and about 6, although the pH can be higher if alkalophilic cellulases are used. The temperature of the hydrolysis is 40° C. to 65° C. unless thermophilic cellulases are used so that higher temperatures can be utilized.

The enzymatic hydrolysis can be carried out with any type of cellulase enzymes capable of hydrolyzing the cellulose to glucose, regardless of their source. Among the most widely studied, characterized and commercially produced cellulases are those obtained from fungi of the genera *Aspergillus*, *Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Schulein et al., *Proceedings of the Second TRICEL Symposium on Trichoderma reesei Cellulases and Other Hydrolases*, Espoo 1993, P. Suominen and T. Reinikainen, Eds. Foundation for Biotechnical and Industrial Fermentation Research, Helsinki 8:109-116, which is incorporated herein by reference).

The enzymatic hydrolysis is carried out in batch, fed batch, or continuous systems. The hydrolysis system may be mixed or unmixed, or mixed part of the time or only in some regions or reactors. The hydrolysis may be carried out as a single stage operation or a multistage operation. The solids consistency during hydrolysis may be 5% to 25% on a weight basis. The cellulase enzyme dosage may be 3 to 50 mg cellulase per gram cellulose. The hydrolysis is run for a time period of 3 to 200 hr. The volume of a hydrolysis vessel is 100,000 to 4 million liters.

Following cellulose hydrolysis of the pretreated feedstock slurry, any insoluble solids, including, but not limited to lignin, present in the resulting sugar stream may be removed using conventional solid-liquid separation techniques prior to any further processing. These solids may be burned to provide energy for the entire process. However, it should be appreciated that lignin may be removed at other stages of the process.

The sugar stream may then be fermented by microbes to produce a fermentation broth comprising a fermentation product. As used herein and as would be familiar to those of skill the art, the terms "fermentation broth" and "fermentation stream" are interchangeable. According to one embodiment of the invention, the fermentation broth is the aqueous stream sent to the stripper for carboxylic acid recovery.

For ethanol production, the fermentation may be carried out with a *Saccharomyces* spp. yeast. Preferably, glucose and any other hexoses typically present in the sugar stream are fermented to ethanol by wild-type *Saccharomyces cerevisiae*, although genetically modified yeasts may be employed as well. For example, if pentose and hexose sugars are present, the fermentation may be performed with a recombinant *Saccharomyces* yeast that is engineered to ferment both hexose and pentose sugars to ethanol. Recombinant yeasts that can ferment the pentose sugar, xylose, to ethanol are described in U.S. Pat. No. 5,789,210, the contents of which are herein incorporated by reference. Furthermore, the pentose sugars, arabinose and xylose, may be converted to ethanol by the yeasts described in Boles et al. (WO 2006/096130, which is incorporated herein by reference).

It is understood by those skilled in the art that the fermentation microbes can produce and/or consume acetic acid. The concentration of acetic acid fed to the fermentation is therefore not necessarily equal to that in the product of the fermentation.

Examples of other fermentation products included within the scope of the invention include sorbitol, butanol, 1,3-propanediol and 2,3-butanediol. Other microorganisms that may be employed in the fermentation include wild-type or recombinant *Escherichia*, *Zymomonas*, *Candida*, *Pichia*, *Streptomyces*, *Bacillus*, *Lactobacillus* and *Clostridium*.

In practice, the fermentation is performed at or near the temperature and pH optima of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The pH of a typical fermentation employing *Saccharomyces cerevisiae* is between about 3 and about 6. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The sugar stream may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using a series of reactors, such as 1 to 6. The fermentation microorganisms may be recycled back to the fermentor or may be sent to distillation without recycle.

It should be understood that the hydrolysis and fermentation reactions can be conducted simultaneously in the same reactor, although it is preferred that the hydrolysis and fermentation are performed separately to achieve the optimal temperature for each process.

The fermentation broth that is sent to distillation is a dilute alcohol solution containing solids, including unconverted cellulose, and any components added during the fermentation to support growth of the microorganisms. Microorganisms are potentially present depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a higher boiling point than water, as is the case when ethanol is distilled.

In embodiments wherein ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns. In this case, dilute beer is sent to the beer column where it is partially concentrated. From the beer column, the vapour goes to a rectification column for further purification. Alternatively, a distillation column is employed that comprises an integral enriching or rectification section. After distillation, the water remaining may be removed from the vapour by a molecular sieve resin, by adsorption, or other azeotrope-breaking methods familiar to those of skill in the art. The vapour may then be condensed and denatured.

An aqueous stream(s) remaining after ethanol distillation and containing solids, referred to herein as "still bottoms", is withdrawn from the bottom of one or more of the column(s) of the distillation unit. The volatile carboxylic acid(s) in this still bottoms stream may then be recovered by the stripper-extractor process of the present invention. This stream will contain the volatile carboxylic acid, inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream". The overhead stream can contain volatile carboxylic acids and is condensed prior to recovery of the carboxylic acid by the stripper-extractor process described herein.

The term "organic solvent" refers to the liquid that extracts the carboxylic acid vapour in the steam stripping stream. The word "organic' in this context means that the solvent is entirely or almost entirely composed of one or more chemical compounds whose molecules contain carbon, except for simple oxides, carbonates, cyanides, and pure carbon. The organic solvent is a solvent for the volatile carboxylic acid, which means it dissolves at least 50 g/L of the volatile carboxylic acid (w/v) at ambient temperature.

Preferably, the organic solvent has a much higher affinity for the volatile carboxylic acid than water. The affinity of the solvent for the volatile carboxylic acid is quantified by the Distribution Coefficient, D. This is measured at a temperature of 30° C. or 50° C. by contacting equal volumes of organic solvent and aqueous stream containing, for example, 10 to 20 g/L of the volatile carboxylic acid and mixing gently to reach equilibrium, which may require up to about 1 hour. The concentration of the volatile carboxylic acid is then determined in the aqueous phase and the organic phase. D is the ratio of the volatile carboxylic acid concentration in the organic phase to that in the aqueous phase. Preferably, D is greater than 5. More preferably, D is greater than 50, most preferably greater than 100. If D is much lower than these values, a large amount of the organic solvent is required to extract the volatile carboxylic acid, and this adds to the cost of the process.

The volatile carboxylic acid is extracted with an organic solvent that is insoluble in water. When referring herein to the organic solvent as "insoluble in water", it is meant that it has a solubility that is less than 5% by weight in water. In embodiments of the invention the solubility may be less than 2% by weight, less than 1% by weight or less than 0.3% by weight. Most preferably, the organic solvent has zero solubility in water. For example, the solubility of the organic solvent in water may be less than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or 0% (w/w) at 100° C.

If the solvent is soluble in water, some of the organic solvent will be lost to the steam phase. This would be a significant drawback to the process as it would complicate recovery of the organic solvent for reuse in the process. That is, if solvent is present in the steam phase it has to be recovered or it is lost and must be replaced with fresh solvent, which is costly. By using an organic solvent that is insoluble with water, this removal step is avoided.

Furthermore, in embodiments of the invention, water is insoluble (zero solubility) or has low solubility in the organic solvent, such as less than 10% by weight, or more preferably less than 3% by weight. Such an embodiment is advantageous as the presence of less water in the solvent phase simplifies recovery of the volatile carboxylic acid. For example, the solubility of water in the organic solvent may be less than 10, 9, 8, 7, 6, 5, 4, 3, 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or 0% (w/w) at 100° C.

The organic solvent has a boiling point at atmospheric pressure that is at least 150° C. For example, the organic solvent may have a boiling point between 150° C. and 650° C. or more typically between 150° C. and 450° CC.

The stripping column and the extractor column preferably operate at roughly the same temperature because steam travels back and forth between the two columns. A temperature range of about 60° C.-175° C., or any temperature therebetween, can be employed in the steam stripping and/or the extracting operations, which temperature is measured under the operating pressure of the steam stripper and/or the extractor, which may be greater than atmospheric, atmospheric or under vacuum. For example, the temperature may be 60, 65, 70, 75, 80, 85, 90, 95, 100, 105, 110, 115, 120, 125, 130, 135, 140, 145, 150, 155, 160, 165, 170 or 175° C. A suitable operating temperature and pressure may be selected based on the design considerations set out in more detail hereinafter. Typically, the steam temperature will be the highest in the steam feed and will decrease as the steam ascends the stripping and extraction columns.

In embodiments of the invention, the steam stripper and the extractor columns are operated at temperatures that are high enough to avoid significant condensation of water. When operated at or near atmospheric pressure, the boiling point of water is 100° C., and the stripper and extractor are thus preferably maintained above this temperature to avoid such condensation. Preferably, the temperature of the steam fed to the stripper is about 110° C. to about 135° C. during atmospheric pressure operation. This temperature is high enough to maintain the steam in the vapor phase, while low enough to be readily available in a plant. More preferably, the temperature of the steam is about 110° C. to about 130° C. It should be understood that small amounts of water can condense during the extraction and form a separate phase. However, these small quantities of water can be easily removed from the organic phase by decanting or other means. Notably, small quantities of water formed from the steam during the steam stripping simply dilute the aqueous stream.

The extraction is preferably performed at a temperature that is low enough so that significant amounts of the organic solvent are not volatilized. Since the organic solvent has an atmospheric boiling point of at least about 150° C., if the operating temperature (at atmospheric pressure) is at or less than 150° C., losses of the solvent to evaporation are reduced or prevented. More preferably, the temperature is well below 150° C., such as a temperature below about 130° C. However, when the extraction is performed under vacuum, the temperature can be as low as about 60° C.

In view of the foregoing, a preferred operating temperature when the carboxylic acid is extracted at atmospheric pressure would be between about 100° C. and about 150° C. or between about 100° C. and about 130° C. For example, the operating temperature of the extraction at atmospheric pressure may be 100, 102, 103, 104, 105, 106, 107, 108, 109, 110, 111, 112, 113, 114, 115, 116, 117, 118, 119, 120, 121, 122, 123, 124, 125, 130, 135, 140, 145, 149 or 150° C. Advantageously, these temperatures are below the boiling point of the organic solvent, at or above the boiling point of water and not significantly above the boiling point of the carboxylic acid at atmospheric pressure. As mentioned previously, the operating temperature may be lower than these values if the extracting step is conducted under vacuum.

An extraction pressure higher than atmospheric has the advantage that the density of the vapour phase is higher, which decreases the size of the distillation equipment. However, the higher pressure requires steam at higher pressure to heat the system, and the high pressure steam is expensive. In addition, the solvent may have limited stability at the higher temperature. Operation under vacuum reduces the temperature and the steam pressure required, and can preserve the stability of the solvent. However, the lower density of the vapour phase increases the size of the equipment required. In addition, if the boiling point of the carboxylic acid is well below 100° C. at the operating pressure, a source of chilled water might be required, which adds to the operating cost of the process. A person of skill in the art could weigh the advantages and disadvantages of operating under pressures above atmospheric, at atmospheric pressure or under vacuum and chose a pressure that is appropriate for the extraction at hand. That is, the invention is not constrained by the operating pressure of the extraction.

Furthermore, there is a risk of loss of the carboxylic acid from the organic solvent at temperatures well above its boiling point. Thus, it is preferable to conduct the extraction at temperatures that are not significantly above the boiling point of the volatile carboxylic acid.

Since the boiling point of acetic acid is 118° C. at atmospheric pressure, it is preferable to operate the extraction below about 130° C. (at atmospheric pressure) when this acid is recovered to avoid significant loss of acetic acid. Thus, in those embodiments where acetic acid is recovered, the temperature of the acetic acid extraction at atmospheric pressure is preferably higher than 100° C. and below 130° C., or any temperature therebetween. For example, the temperature at atmospheric pressure may be 100, 101, 102, 103, 104, 105, 106, 107, 108, 109, 110, 111, 112, 113, 114, 115, 116, 117, 118, 119, 120, 121, 122, 123, 124, 125, 126, 127, 128, 129 or 130° C.

The steam containing carboxylic acid must be in contact with the solvent for a sufficient time to be extracted by the solvent. This is preferably one second to a few seconds per stage.

Representative examples of organic solvents that may possess the foregoing properties include aliphatic amines having at least 10 carbon atoms. An example of a suitable aliphatic amine is, but is not limited to, tributylamine, tripentylamine, trihexylamine, trioctylamine, tridecylamine or mixtures thereof. Preferred mixtures of aliphatic amines are mixtures of trioctylamine and tridecylamine in ratios of 70/30, respectively, to 30/70, respectively. A commercial product that is a mixture of aliphatic amines is Alamine® 336, which is an organic solvent commercially available from Cognis that contains a ratio of trioctylamine to tridecylamine of 2/1.

Optionally, the organic solvent includes a co-solvent such as a phenol or a naphthol to facilitate phase separation and selectivity for the volatile carboxylic acid. The phenol or naphthol may be alkylated, having 1 to 40 carbon atoms in the alkyl group. An example of a suitable phenol is nonylphenol. This compound is available commercially as p-nonylphenol from Schenectady International. Another suitable phenol is octylphenol. Non-limiting examples of suitable naphthols are 1-naphthol and 2-naphthol.

Preferably, if a phenol is utilized as a co-solvent in combination with one or more aliphatic amines, the mixture of the phenol and one or more aliphatic amines may contain 40 wt % to 80 wt % of the phenol with the balance of the mixture being the aliphatic amine(s).

Amines that are particularly suitable for use in the invention include tridecylamine or trioctylamine that each have a solubility in water of less than 5 parts per million (ppm) and boiling points that are roughly 350° C. Nonylphenol has a solubility in water of 0.08% at 22° C. and an atmospheric boiling point of 300° C. and thus is also particularly suitable for use in the invention. However, the practice of this invention is not constrained by the use of any particular compound or compounds making up the organic solvent. That is, other organic solvents may be selected with similar or other desirable properties.

In one embodiment of the invention, the recovery of the carboxylic acid in accordance with the present invention is carried out using two columns, each containing stages for the contacting of steam and liquid streams. According to this embodiment, vapourization of the carboxylic acid occurs in the first column, which is known as the stripping column, while extraction with the organic solvent occurs in the second column, which is known as the extraction column.

The two columns each contain one or more stages. Typically, the carboxylic acids one would recover in accordance with the invention have boiling points and volatilities of the same magnitude as water, although other carboxylic acids can be recovered that do not possess these properties. In those embodiments in which the carboxylic acid that is recovered has a boiling point and volatility that is similar to that of water, only a partial removal of the acid takes place in a single contacting between water and steam. Such a process would generally not be efficient with a single stage, so typically more than one extracting stage would be conducted, and even more preferably, the consecutive contacting stages in the stripping columns is 5 to 75. A more preferred number of stages is 10 to 40. The number of stages in the two columns is typically the same, but it need not be.

The steam stripping is conducted by introducing the aqueous feed stream (also referred to herein simply as an "aqueous stream") comprising the carboxylic acid at or near the top of the stripping column and steam at or near the bottom. Steam flows upwardly and countercurrent to the aqueous feed stream and volatilizes the carboxylic acid, thereby producing a vapour stream comprising vapourized carboxylic acid and steam and a remaining aqueous stream that has been stripped, also referred to herein as a "stripped aqueous stream". The vapour stream generated in the first stripping column is then fed to the extraction column. The extraction column typically comprises a series of extraction stages where organic solvent is introduced at the top, flows downward, and is contacted with the vapour stream comprising the carboxylic acid from the stripping column. The solvent extracts the carboxylic acid from the vapour stream, which produces a stream comprising the organic solvent and the carboxylic acid, (also referred to herein as a "solvent stream" or a "solvent carboxylic acid" stream). The steam that exits the extraction column, also referred to herein as a "clean steam" or a "steam product stream", is now at least substantially depleted of the carboxylic acid and is sent back to the stripping column to further extract the carboxylic acid. Ultimately, the streams exiting the system are the stripped aqueous stream at least substantially depleted of the carboxylic acid, the clean steam, and the solvent stream containing the organic solvent and the carboxylic acid. As mentioned hereinafter, the stripping and extracting columns can be one integral unit.

By "at least substantially depleted of the carboxylic acid", with reference to the carboxylic acid content of the steam produced by the extracting, it is meant that such steam contains less than 40% of the carboxylic acid concentration as the steam carried into the extraction. In another embodiment, the stream from the extracting contains less than 10% of the carboxylic acid concentration as the steam carried into the extraction. In a most preferred embodiment, the steam from the extraction contains less than 2% of the carboxylic acid concentration as the steam carried into the extraction. The aforementioned phrase, with reference to the carboxylic acid content of the stripped aqueous stream, means that such stripped aqueous stream exiting the stripping column contains less than 50% the concentration of the carboxylic acid as was fed to the stripping column. More preferably, the stripped aqueous stream contains less than 15% the concentration of the carboxylic acid as was fed to the stripping column.

After the extracting step, the carboxylic acid is separated from the organic solvent. In one embodiment of the invention, the carboxylic acid has a significantly lower boiling point than the organic solvent, thereby allowing these two components to be easily separated from one another by heating. That is, the carboxylic acid can be heated to boil while the organic solvent does not. This heating can be carried out by evaporation or distillation.

In those embodiments in which acetic acid is separated from the organic solvent at atmospheric pressure, such separation is preferably at a temperature that is higher than about 118° C. and lower than the boiling point of the solvent. When acetic acid is separated from a nonylphenol and mixed triamine solvent, the separation is preferably carried out by heating to a temperature of about 180° C. to about 240° C. at atmospheric pressure. More preferably, the temperature is about 190° C. to about 210° C. at atmospheric pressure.

Without intending to be limiting, in practice, several factors can be taken into consideration to achieve optimal separation, while minimizing cost. For instance, at pressures other than atmospheric, the temperature is generally chosen so as to be above the boiling point of the volatile carboxylic acid and below that of the solvent at the operating pressure. A pressure higher than atmospheric has the advantage that the density of the vapour phase is higher, which decreases the size of the distillation or evaporation equipment. However, the higher pressure requires steam at higher pressure to heat the system, and the high pressure steam is expensive to produce. In addition, the solvent may have limited stability at the higher temperature. Operation under vacuum reduces the temperature and the steam pressure required, and can preserve the stability of the solvent. However, the lower density of the vapour phase increases the size of the equipment required. In addition, if the boiling point of the volatile carboxylic acid is well below 100° C. at the operating pressure, a source of chilled water might be required, which adds to the operating cost of the process.

If the volatile carboxylic acid is separated from the solvent by distillation, the distillation column can consist of trays or packing. Any suitable tray or packed column can be utilized in accordance with the invention, although the following factors may be taken into consideration when making an appropriate selection. For instance, a tray column may be preferred, as it is less expensive. On the other hand, a packed column, which can contain random packing or structured packing, has a lower pressure drop and a higher efficiency than a tray column. However, the packing is susceptible to fouling by particulates in the process streams or by products from degradation reactions. Packed columns also require distributors and collectors in each stage, which adds to the cost. A person of skill in the art could weigh the advantages and disadvantages of using a tray or packed column and accordingly choose one appropriate for the separation at hand.

After separation by heating or distillation, the volatile carboxylic acid vapour is condensed to produce a concentrated stream of the volatile carboxylic acid. If the volatile carboxylic acid is produced by distillation, the condenser can be at the top of the distillation column or can be located at or near the ground. The carboxylic acid vapour can be condensed in the presence of water, if desired. In one advantageous embodiment of the invention, the amount of water present is low enough so that it does not dilute the acid to such an extent that it makes the water expensive to remove. A preferred amount of water present is 0% to 50% of the weight of acid. After removal of the volatile carboxylic acid from the organic solvent, the organic solvent can be reused in the extractor. If there are contaminants present in the carboxylic acid, a second distillation can be run to further purify the product.

The present invention will be further illustrated in the following examples. However, it is to be understood that these examples are for illustrative purposes only, and should not be used to limit the scope of the present invention in any manner.

An embodiment of the invention is described below with reference to FIG. 1, which for simplicity contains a stripping column and an extraction column containing two stages each. However, the principles are applicable to systems with more than two stages. For ease of reference, it should be noted that in FIG. 1, the first stripping stage is at the bottom of the column, while the second stripping stage is at the top. The extracting stages are depicted in a similar manner.

The aqueous feed stream 10 comprises the carboxylic acid, in this case acetic acid. This stream 10 is fed at the top of the stripping column, which is the second stripping stage 25. Clean steam 70 is introduced at the bottom of the stripping column, in this case to the first stripping stage 50 of the stripping column. The clean steam 70 flows upwardly and countercurrent to an aqueous stream 40 and volatilizes acetic acid contained therein in the first stripping stage 50, thereby producing a vapour stream 110 comprising vapourized acetic acid and steam. The vapour stream 110 is then fed to a first extraction stage 160 of the extraction column. The first extraction stage 160 also receives a solvent stream 150 comprising the solvent and acetic acid flowing down from a second extraction stage 140. In the first extraction stage 160, the acetic acid vapour in vapour stream 110 is extracted with the solvent in solvent stream 150. The resulting clean steam 100, which is at least substantially depleted of the acetic acid, is sent to the second stripping stage 25. A solvent stream 190 containing the acetic acid and the organic solvent exits the first extraction stage 160. A portion of this solvent stream 190 is sent back to feed the second extraction stage as solvent recycle stream 170. The balance of the solvent stream 190 is a solvent acetic acid stream 180 that is sent for further processing, which could include separating the acetic acid from the solvent.

The clean steam 100 is fed to the second stripping stage 25, along with the aqueous feed stream 10. The clean steam 100 strips a portion of the acetic acid from the aqueous feed stream 10, resulting in the aqueous stream 40, which has a reduced level of acetic acid, and vapour stream 30 containing vapourized acetic acid and steam. The aqueous stream 40 is fed to the first stripping stage 50, where it is contacted with the clean steam 70 as described above. This produces aqueous stream 60, which is the stripped aqueous process stream that exits the system. This stream is significantly depleted of acetic acid relative to aqueous feed 10 and is suitable for further processing. For example, if this stream contains sugar, it may be fermented to ethanol.

Vapour stream 30 containing volatilized acetic acid and steam is fed to the second extraction stage 140 along with a solvent stream 130 that is a combination of a fresh solvent feed 120 and the solvent recycle stream 170 described previously. Solvent stream 130 extracts a portion of the acetic acid in vapour stream 30 to form the solvent stream 150, which, in turn, is fed to the first extraction stage 160. The acetic acid in vapour stream 30 has acetic acid largely removed therefrom by extraction in the second extraction stage 140 and the clean steam exits the system as the steam product stream 200. This steam product stream 200 is recycled to feed stream 70. Optionally it can be used elsewhere in the process.

In a system with more than two stages, the flows proceed as shown in FIG. 1, with stream 70 introduced at the bottom of the stripping column, and the steam flowing upwardly back and forth between the stripping and extraction columns through a predetermined number of stages and finally exiting as steam product 200 at the top of the extraction column.

A person of skill in the art can select any suitable flow rate for a given stream within the system. In practice, several factors, such as those set forth below, will have a bearing on the flow rates that are chosen.

Typically, the flow rates of aqueous feed 10, clean steam 70, and solvent stream 130 are chosen based on the process flow of aqueous feed 10, the amount of steam and solvent required to remove the carboxylic acid, and the requirement of a stable operation. The process flow of aqueous feed 10 is set by the requirements of the overall plant operation. The flow of clean steam 70 is typically 1% to 20% of the flow of aqueous feed 10, on a mass basis. A lower steam flow could be inadequate to strip the carboxylic acid, while a higher steam flow is costly in the production of the steam. More preferably, the steam flow is 5% to 15% of the process flow.

The solvent flow into the extractor column is of the same magnitude, on a mass basis, as the aqueous feed 10 to the stripper column. The solvent flow to the extractor is typically 50% to 150% of the aqueous feed flow. In one particularly advantageous embodiment of the invention, a portion of the solvent that exits the bottom of the extractor column is recycled back to the solvent feed (as shown in FIG. 1 and described previously), thereby decreasing solvent costs. The ratio of recycled solvent is preferably 85% to 95%.

The column diameter, number of stages, and stage packings and sizes can be chosen based on the guidelines set forth in Example 1. The choices are made to achieve a stable operation without flooding of individual stages and to achieve the maximum efficiency of the mass transfer between the steam and the aqueous and solvent streams. The stages are also typically designed to avoid the carry-over of liquids with the steam between stages, such as by the use of demisters.

Although two column systems have been described, the recovery of carboxylic acid can be carried out in a structure that is a single physical column having therein a series of alternating stripping and extraction stages. In such a system, the liquid flow through the column is such that the aqueous feed stream comprising the carboxylic acid flows only through the acid stripping stages while the organic solvent flows only through the extraction stages. This may be achieved by conventional downcomers that direct the aqueous feed stream downwardly from one stripping stage to the next and the organic solvent from one extraction stage to the next. These downcomers may be disposed internally or externally of the stripping column.

Figure 2:
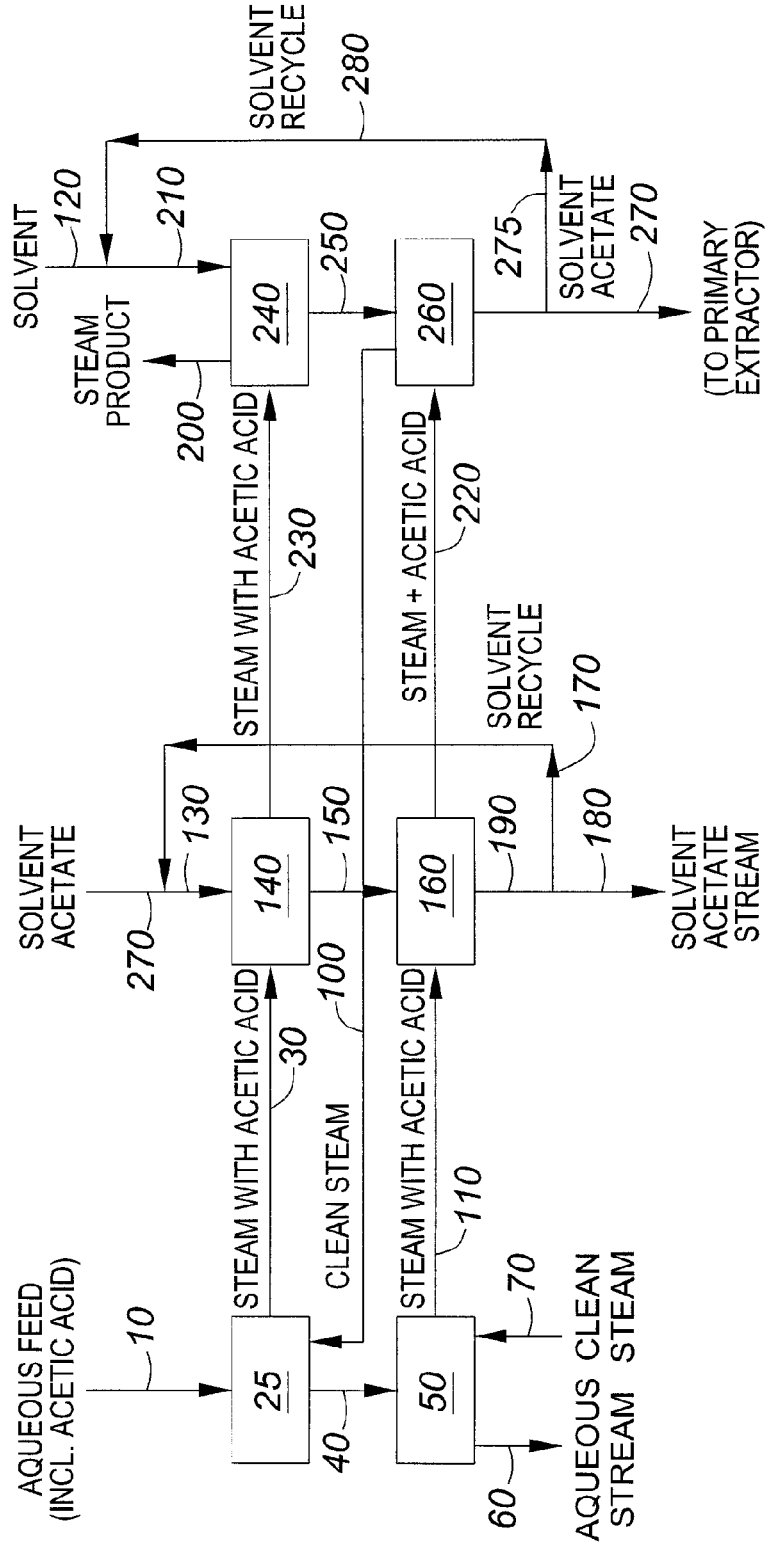
FIG. 2 is a process flow diagram for recovering a volatile carboxylic acid according to another embodiment of the invention.

In yet a further embodiment of the invention, the system comprises a stripping column and two or more extraction columns. The flowsheet of a system of a stripping column with two extraction columns, referred to herein as primary and secondary extraction columns, is shown in FIG. 2.

The aqueous feed stream 10 comprises the carboxylic acid, in this case acetic acid. This aqueous feed stream 10 is fed at the top of the stripping column, which is the second stripping stage 25. Clean steam 70 is introduced at the bottom of the stripping column, in this case to the first stripping stage 50 of the stripping column. Steam flows upwardly and countercurrent to an aqueous stream 40 and volatilizes acetic acid contained therein in the first stripping stage 50 of the stripper column, thereby producing a vapour stream 110 comprising vapourized acetic acid and steam. This vapour stream 110 is then fed to the first extraction stage 160 of the primary extraction column. The first extraction stage 160 of the primary extraction column also receives a solvent stream 150 comprising solvent and acetic acid flowing down from the second extraction stage 140 of the primary extraction column. In the first extraction stage 160, the acetic acid vapour in vapour stream 110 is extracted with the solvent in solvent stream 150. The steamstream 220 produced from the first extraction stage 160 then has only a low level of acetic acid and is sent to the first extraction stage 260 of the secondary extraction column. A solvent stream 190 containing acetic acid and the organic solvent exits the first extraction stage 160 of the primary extraction column. A portion of this solvent stream 190 is sent back to feed the primary extraction column as solvent recycle stream 170. The balance of the solvent stream 190 is a solvent acetic acid stream 180 that is sent for further processing, which could include separating the acetic acid from the solvent.

The steam stream 220, containing low levels of acetic acid, is fed to the first extraction stage 260 of the secondary extraction column, along with solvent stream 250 that contains acetic acid from the extraction carried out in the second extraction stage 240. The solvent in solvent stream 250 extracts the acetic acid from the steam stream 220 and produces the solvent stream 275 from the secondary extractor. A portion of solvent stream 275 is recycled back to feed the second extraction stage 240 of the secondary extractor as solvent recycle stream 280. The balance of solvent stream 275, namely solvent acetic acid stream 270, is sent to the primary extractor to be combined with recycle solvent 170 to feed the second stage 140 of this extractor.

Clean steam 100 exiting the first extraction stage 260 of the secondary extractor has only a very low concentration of acetic acid. Clean steam 100 and aqueous feed stream 10 are fed to the second stripping stage 25. The steam strips a portion of the acetic acid from the aqueous feed 10, resulting in aqueous stream 40 with a reduced level of acetic acid, and vapour stream 30 containing volatilized acetic acid and steam. Aqueous stream 40 is fed to first stripping stage 50, where it is contacted with clean steam 70 as described above. This produces aqueous stream 60, which is the stripped aqueous stream that exits the system. This stream has a reduced level of acetic acid relative to aqueous feed 10 and is suitable for further processing. For example, if such stream contains sugar, it may be fermented to ethanol.

Vapour stream 30 containing volatilized acetic acid and steam is fed to the second extraction stage 140 in the primary extractor along with a solvent stream 130. Solvent stream 130 is the combination of the solvent acetate stream 270 from the secondary extractor and solvent recycle stream 170. Solvent stream 130 extracts a portion of the acetic acid from vapour stream 30 to form solvent stream 150, which is fed to the first extraction stage 160. Vapour stream 30 has its acetic acid mostly removed by extraction in second extraction stage 140 and this results in steam stream 230, which is the steam containing residual acetic acid that feeds the second extraction stage 240 in the secondary extraction column. The steam stream exits the system as the steam product stream 200 after contacting the solvent in this extraction stage. This steam product stream 200 is recycled to clean steam 70 or optionally can be used elsewhere in the process.

EXAMPLES

Example 1

Two-Column Stripper-Extractor for Removal of Acetic Acid from Water

This example describes the mass flows and specifications of a 36-stage stripper-extractor system for the recovery of acetic acid from an aqueous feed stream.

The aqueous feed stream contains 5.0 g/L acetic acid and is fed to the top (stage 36) of the stripper column at a rate of 316,050 L/hr (316.0 m$^3$/hr). Steam is fed to the bottom (stage 1) at 12% of the aqueous feed rate, which is 37,926 kg/hr (37.9 t/hr). The solvent is a 30/70 mixture of Alamine® 336 in nonylphenol. The overall feed rate to the top (stage 36) of the extractor matches that of the aqueous feed stream of 316,050 L/hr (316.0 m$^3$/hr). This feed consists of 15,802 L/hr (15.8 m$^3$/hr) of fresh solvent feed and 300,247 L/hr (300.2 m$^3$/hr) of solvent recycle. The recycle fraction is therefore 95%.

The mass flows and degree of stripping and extraction of acetic acid are determined based on the relative volatility of acetic acid and steam (for the stripping reaction) and the distribution coefficient of acetic acid between the solvent and water. The relative volatility of acetic acid and water is about 0.6 and this value is used in this example. The distribution coefficient D between the solvent and water, which is the concentration of acetic acid in the solvent divided by that in water, is about 100. It is assumed that all stages reach equilibrium, as further discussed below.

The mass flows and acetic acid concentrations are shown in Table 1 and Table 2 below. The process stream at stage 1 in the stripping column (Table 1) contains 1.40 g/L acetic acid, so 72% of the acetic acid is recovered. The solvent exiting the bottom of the extraction column contains 70.28 g/L of acetic acid (Table 2). This is a large increase in concentration compared with the 5 g/L feed concentration. The steam exiting the top of the extraction column contains only 0.7 g/L acetic acid (Table 2).

TABLE 1

Process flows in the stripping column of a two column stripper-extractor for acetic acid recovery

| | Aqueous phase | | Steam phase | |
|---|---|---|---|---|
| | | | Steam | |
| Stage | Process (m$^3$/h) | Acetic acid (g/L) | (t/h) | Acetic acid (g/L) |
| Feed | 316.0 | 5.0 | | |
| 36 | 316.0 | 4.74 | 37.9 | 2.84 |
| 35 | 316.0 | 4.50 | 37.9 | 2.70 |
| 34 | 316.0 | 4.27 | 37.9 | 2.56 |
| 33 | 316.0 | 4.06 | 37.9 | 2.43 |
| 32 | 316.0 | 3.86 | 37.9 | 2.32 |
| 31 | 316.0 | 3.68 | 37.9 | 2.21 |
| 30 | 316.0 | 3.51 | 37.9 | 2.10 |
| 29 | 316.0 | 3.35 | 37.9 | 2.01 |
| 28 | 316.0 | 3.20 | 37.9 | 1.92 |
| 27 | 316.0 | 3.06 | 37.9 | 1.84 |
| 26 | 316.0 | 2.93 | 37.9 | 1.76 |
| 25 | 316.0 | 2.81 | 37.9 | 1.69 |
| 24 | 316.0 | 2.70 | 37.9 | 1.62 |
| 23 | 316.0 | 2.60 | 37.9 | 1.56 |
| 22 | 316.0 | 2.50 | 37.9 | 1.50 |
| 21 | 316.0 | 2.41 | 37.9 | 1.45 |
| 20 | 316.0 | 2.33 | 37.9 | 1.40 |
| 19 | 316.0 | 2.25 | 37.9 | 1.35 |
| 18 | 316.0 | 2.17 | 37.9 | 1.30 |
| 17 | 316.0 | 2.11 | 37.9 | 1.26 |
| 16 | 316.0 | 2.04 | 37.9 | 1.23 |
| 15 | 316.0 | 1.98 | 37.9 | 1.19 |
| 14 | 316.0 | 1.93 | 37.9 | 1.16 |
| 13 | 316.0 | 1.88 | 37.9 | 1.13 |
| 12 | 316.0 | 1.83 | 37.9 | 1.10 |
| 11 | 316.0 | 1.78 | 37.9 | 1.07 |
| 10 | 316.0 | 1.74 | 37.9 | 1.05 |
| 9 | 316.0 | 1.70 | 37.9 | 1.02 |
| 8 | 316.0 | 1.67 | 37.9 | 1.00 |
| 7 | 316.0 | 1.63 | 37.9 | 0.98 |
| 6 | 316.0 | 1.60 | 37.9 | 0.96 |
| 5 | 316.0 | 1.57 | 37.9 | 0.94 |
| 4 | 316.0 | 1.55 | 37.9 | 0.93 |
| 3 | 316.0 | 1.52 | 37.9 | 0.91 |
| 2 | 316.0 | 1.50 | 37.9 | 0.90 |
| 1 | 316.0 | 1.40 | 37.9 | 0.84 |

TABLE 2

Process flows in the extraction column of a two column stripper-extractor for acetic acid recovery

| Stage | Solvent ($m^3$/h) | Steam acetic acid (g/L) | Solvent acetic acid (g/L) |
|---|---|---|---|
| Feed | 15.8 | 0 | 0.00 |
| Recycle | 300.2 | 0.70 | 70.28 |
| Net feed | 316.0 | 0.67 | 66.77 |
| 36 | 316.0 | 0.67 | 67.03 |
| 35 | 316.0 | 0.67 | 67.27 |
| 34 | 316.0 | 0.67 | 67.50 |
| 33 | 316.0 | 0.68 | 67.71 |
| 32 | 316.0 | 0.68 | 67.90 |
| 31 | 316.0 | 0.68 | 68.09 |
| 30 | 316.0 | 0.68 | 68.26 |
| 29 | 316.0 | 0.68 | 68.42 |
| 28 | 316.0 | 0.69 | 68.56 |
| 27 | 316.0 | 0.69 | 68.70 |
| 26 | 316.0 | 0.69 | 68.83 |
| 25 | 316.0 | 0.69 | 68.95 |
| 24 | 316.0 | 0.69 | 69.06 |
| 23 | 316.0 | 0.69 | 69.17 |
| 22 | 316.0 | 0.69 | 69.26 |
| 21 | 316.0 | 0.69 | 69.35 |
| 20 | 316.0 | 0.69 | 69.44 |
| 19 | 316.0 | 0.70 | 69.52 |
| 18 | 316.0 | 0.70 | 69.59 |
| 17 | 316.0 | 0.70 | 69.66 |
| 16 | 316.0 | 0.70 | 69.72 |
| 15 | 316.0 | 0.70 | 69.78 |
| 14 | 316.0 | 0.70 | 69.83 |
| 13 | 316.0 | 0.70 | 69.89 |
| 12 | 316.0 | 0.70 | 69.93 |
| 11 | 316.0 | 0.70 | 69.98 |
| 10 | 316.0 | 0.70 | 70.02 |
| 9 | 316.0 | 0.70 | 70.06 |
| 8 | 316.0 | 0.70 | 70.09 |
| 7 | 316.0 | 0.70 | 70.13 |
| 6 | 316.0 | 0.70 | 70.16 |
| 5 | 316.0 | 0.70 | 70.19 |
| 4 | 316.0 | 0.70 | 70.21 |
| 3 | 316.0 | 0.70 | 70.24 |
| 2 | 316.0 | 0.70 | 70.26 |
| 1 | 316.0 | 0.70 | 70.28 |
| Product | 15.8 | 0.70 | 70.28 |
| Recycle | 300.2 | 0.70 | 70.28 |

The mass flows and concentrations shown in Table 1 and Table 2 are achieved with the appropriate design of the stripper and extractor columns and stages. These design details are described in more detail below and in Table 3. In the last column of Table 3, reference is made to tables and figures, which can be found in Chemical Engineers' Handbook, Perry and Chilton, $5^{th}$ edition, 1973 (referred to herein as "Perry and Chilton").

TABLE 3

Design details of a 36-stage two column stripper-extractor.

| Column specifications | Stripping column | | Extractor column | | Reference |
|---|---|---|---|---|---|
| | Process | Steam | Steam | Solvent | |
| Diameter (inches) | 132 | 132 | 132 | 132 | |
| Flow (t/h) | 316.0 | 37.9 | 37.9 | 316.0 | |
| Density (g/mL) | 1.02 | 0.000721 | 0.000721 | 1.02 | |
| Flow ($m^3$/h) | 310 | 52591 | 52591 | 351 | |
| Flow ($ft^3$/sec) | 3.04 | 516.20 | 516.20 | 3.45 | |
| Column area ($ft^2$) | 94.99 | 94.99 | 94.99 | 94.99 | |
| Packing | 1 inch steel Pall rings | | 1 inch steel Pall rings | | |
| Packing void (%) | 94.00 | 94.00 | 94.00 | 94.00 | Table 18-6 |
| Openings (%) | 35.00 | 35.00 | 35.00 | 35.00 | |
| Section flow (ft/s) | 0.03 | 5.78 | 5.78 | 0.04 | |
| Orifice flow (ft/s) | 0.09 | 15.53 | 15.53 | 0.10 | |
| Coarse flooding calculation | | | | | |
| L/G factor | 0.22 | | 0.22 | | |
| Minimum | 0.005 | | 0.005 | | FIG. 18-38 |
| Maximum | 0.4 | | 0.4 | | |
| Flooding calculation | | | | | |
| Flooding factor | 0.08 | | 0.08 | | FIG. 18-39 |
| Packing factor | 48 | | 48 | | Table 18-5 |
| Flooding G (lb/s/$ft^2$) | 0.388 | | 0.388 | | FIG. 18-39 |
| Flooding G (ft/s) | 8.63 | | 8.63 | | FIG. 18-39 |
| Percent of flooding | 67.02 | | 67.02 | | |
| Packing Delta P (in/ft) | 0.80 | | 0.80 | | FIG. 18-39 |
| Mass transfer calculation | | | | | |
| Flow lb/h/$ft^2$ | 7787.45 | | 934.49 | 7787.45 | |
| Vivian factor | 15 | | 7.5 | | FIG. 18-71 |
| Hg (ft) | 0.76 | | 0.38 | | FIG. 18-71 |
| Column size | | | | | |
| Efficiency (%) | 50 | | 50 | | |
| Packing/stage (ft) | 1.52 | | 0.76 | | |
| Number of stages | 36 | | 36 | | |
| Packing height (ft) | 54.65 | | 27.32 | | |

TABLE 3-continued

Design details of a 36-stage two column stripper-extractor.

| Column specifications | Stripping column | | Extractor column | | |
| --- | --- | --- | --- | --- | --- |
| | Process | Steam | Steam | Solvent | Reference |
| Packing volume (ft³) | 5190.92 | | 2595.46 | | |
| Packing Delta P (inches) | 43.72 | | 21.86 | | |

The columns have a diameter of 11 feet (132 inches) each and the packing of each column is composed of 1 inch steel Pall rings. The choice of packing and the flow rates allow the determination of flooding to be made by using the cited sections of Perry and Chilton. Advantageously, the coarse flooding calculation and the fine flooding calculation indicate that the desired flow velocities are within ranges that are not expected to result in flooding of the stages. The mass transfer calculation and the assumption of 50% efficiency of the packing result in each stage of the stripper column being 1.52 feet tall and each stage of the extractor column being 0.76 feet tall. The overall column heights are 55 feet for the stripper column and 27 feet for the extractor column, which is reasonable for use in industry. The pressure drop through the stripper column is 43.7 inches of water pressure and through the extractor column is 21.9 inches of water pressure. The total, 65.6 inches of water pressure, corresponds to just a few pounds per square inch pressure. This implies that the inlet steam temperature is just a few degrees above the outlet steam temperature. The inlet steam temperature could be 120° C.

Example 2

Three-Column Stripper-Extractor for Removal of Acetic Acid from Water

This example describes the mass flows and specifications of a 36-stage stripper-extractor system for the recovery of acetic acid from an aqueous feed stream.

The system described herein has one stripper column and two extractor columns and operates as shown in FIG. 2. The aqueous feed stream contains 5.0 g/L acetic acid and is fed to the top (stage 36) of the stripper column at a rate of 316,050 L/hr (316.0 m³/hr). Steam is fed to the bottom (stage 1) at 12% of the aqueous feed rate, which is 37,926 kg/hr (37.9 t/hr). The solvent is a 30/70 mixture of Alamine® 336 in nonylphenol. The overall feed rate to the top (stage 36) of the primary and secondary extractors is 50% of that of the aqueous feed stream and is 158,025 L/hr (158.0 m³/hr). This feed consists of 7901 kg/hr of fresh solvent feed and 150,124 L/hr (150.1 m³/hr) of solvent recycle. The recycle fraction is therefore 95%.

The mass flows and degree of stripping and extraction of acetic acid are determined based on the relative volatility of acetic acid and steam (for the stripping reaction) and the distribution coefficient of acetic acid between the solvent and water. The relative volatility of acetic acid and water is about 0.6 and this value is used in this example. The distribution coefficient D between the solvent and water, which is the concentration of acetic acid in the solvent divided by that in water, is about 100. It is assumed that all stages reach equilibrium.

The mass flows and acetic acid concentrations are shown in Tables 4, 5 and 6 for the stripping column, primary extraction column and secondary extraction column, respectively. The process stream at stage 1 in the stripping column contains 0.25 g/L acetic acid, so 91% of the acetic acid is recovered. The solvent exiting the bottom of the extraction column contains 67.4 g/L of acetic acid. This is a large increase in concentration compared with the 5 g/L feed concentration. The steam exiting the top of the secondary extraction column contains only 0.0021 g/L acetic acid. Advantageously, the second extraction column increases the recovery of acetic acid from 72% to 91% while decreasing the solvent usage by 50%.

TABLE 4

Process flows in the stripper column of the three-column stripper-extractor

| | Aqueous phase | | Steam phase | |
| --- | --- | --- | --- | --- |
| | | | Steam | |
| Stage | Process (m³/h) | Acetic acid (g/L) | (t/h) | Acetic acid (g/L) |
| Feed | 316.0 | 5.0 | | |
| 36 | 316.0 | 4.66 | 37.9 | 2.80 |
| 35 | 316.0 | 4.35 | 37.9 | 2.61 |
| 34 | 316.0 | 4.06 | 37.9 | 2.44 |
| 33 | 316.0 | 3.79 | 37.9 | 2.27 |
| 32 | 316.0 | 3.53 | 37.9 | 2.12 |
| 31 | 316.0 | 3.30 | 37.9 | 1.98 |
| 30 | 316.0 | 3.07 | 37.9 | 1.84 |
| 29 | 316.0 | 2.87 | 37.9 | 1.72 |
| 28 | 316.0 | 2.68 | 37.9 | 1.61 |
| 27 | 316.0 | 2.50 | 37.9 | 1.50 |
| 26 | 316.0 | 2.33 | 37.9 | 1.40 |
| 25 | 316.0 | 2.17 | 37.9 | 1.30 |
| 24 | 316.0 | 2.03 | 37.9 | 1.22 |
| 23 | 316.0 | 1.89 | 37.9 | 1.13 |
| 22 | 316.0 | 1.76 | 37.9 | 1.06 |
| 21 | 316.0 | 1.65 | 37.9 | 0.99 |
| 20 | 316.0 | 1.54 | 37.9 | 0.92 |
| 19 | 316.0 | 1.43 | 37.9 | 0.86 |
| 18 | 316.0 | 1.34 | 37.9 | 0.80 |
| 17 | 316.0 | 1.25 | 37.9 | 0.75 |
| 16 | 316.0 | 1.16 | 37.9 | 0.70 |
| 15 | 316.0 | 1.09 | 37.9 | 0.65 |
| 14 | 316.0 | 1.01 | 37.9 | 0.61 |
| 13 | 316.0 | 0.95 | 37.9 | 0.57 |
| 12 | 316.0 | 0.88 | 37.9 | 0.53 |
| 11 | 316.0 | 0.82 | 37.9 | 0.49 |
| 10 | 316.0 | 0.77 | 37.9 | 0.46 |
| 9 | 316.0 | 0.72 | 37.9 | 0.43 |
| 8 | 316.0 | 0.67 | 37.9 | 0.40 |
| 7 | 316.0 | 0.62 | 37.9 | 0.37 |
| 6 | 316.0 | 0.58 | 37.9 | 0.35 |
| 5 | 316.0 | 0.54 | 37.9 | 0.33 |
| 4 | 316.0 | 0.51 | 37.9 | 0.30 |
| 3 | 316.0 | 0.47 | 37.9 | 0.28 |
| 2 | 316.0 | 0.44 | 37.9 | 0.27 |
| 1 | 316.0 | 0.41 | 37.9 | 0.25 |

TABLE 5

Process flows in the primary extraction column of the three column stripper-extractor

| Stage | Solvent (m³/h) | Steam acetic acid (g/L) | Solvent acetic acid (g/L) |
|---|---|---|---|
| Second extractor feed | 7.9 | 0 | 0.21 |
| Recycle | 150.1 | 0.67 | 67.39 |
| Net feed | 158.0 | 0.64 | 64.04 |
| 36 | 158.0 | 0.65 | 64.55 |
| 35 | 158.0 | 0.65 | 65.02 |
| 34 | 158.0 | 0.65 | 65.45 |
| 33 | 158.0 | 0.66 | 65.84 |
| 32 | 158.0 | 0.66 | 66.19 |
| 31 | 158.0 | 0.67 | 66.50 |
| 30 | 158.0 | 0.67 | 66.78 |
| 29 | 158.0 | 0.67 | 67.04 |
| 28 | 158.0 | 0.67 | 67.26 |
| 27 | 158.0 | 0.67 | 67.46 |
| 26 | 158.0 | 0.68 | 67.63 |
| 25 | 158.0 | 0.68 | 67.78 |
| 24 | 158.0 | 0.68 | 67.91 |
| 23 | 158.0 | 0.68 | 68.02 |
| 22 | 158.0 | 0.68 | 68.11 |
| 21 | 158.0 | 0.68 | 68.18 |
| 20 | 158.0 | 0.68 | 68.24 |
| 19 | 158.0 | 0.68 | 68.28 |
| 18 | 158.0 | 0.68 | 68.31 |
| 17 | 158.0 | 0.68 | 68.33 |
| 16 | 158.0 | 0.68 | 68.33 |
| 15 | 158.0 | 0.68 | 68.32 |
| 14 | 158.0 | 0.68 | 68.31 |
| 13 | 158.0 | 0.68 | 68.28 |
| 12 | 158.0 | 0.68 | 68.24 |
| 11 | 158.0 | 0.68 | 68.20 |
| 10 | 158.0 | 0.68 | 68.14 |
| 9 | 158.0 | 0.68 | 68.08 |
| 8 | 158.0 | 0.68 | 68.02 |
| 7 | 158.0 | 0.68 | 67.94 |
| 6 | 158.0 | 0.68 | 67.86 |
| 5 | 158.0 | 0.68 | 67.78 |
| 4 | 158.0 | 0.68 | 67.69 |
| 3 | 158.0 | 0.68 | 67.60 |
| 2 | 158.0 | 0.67 | 67.50 |
| 1 | 158.0 | 0.67 | 67.39 |
| Product | 7.9 | 0.67 | 67.39 |
| Recycle | 150 | 0.67 | 67.39 |

TABLE 6

Process flows in the secondary extraction column of the three column stripper-extractor

| Stage | Solvent (m³/h) | Steam acetic acid (g/L) | Solvent acetic acid (g/L) |
|---|---|---|---|
| Feed | 7.9 | 0 | 0.00 |
| Recycle | 150.1 | 0.0021 | 0.21 |
| Net feed | 158.0 | 0.0020 | 0.20 |
| 36 | 158.0 | 0.0020 | 0.20 |
| 35 | 158.0 | 0.0020 | 0.20 |
| 34 | 158.0 | 0.0020 | 0.20 |
| 33 | 158.0 | 0.0020 | 0.20 |
| 32 | 158.0 | 0.0020 | 0.20 |
| 31 | 158.0 | 0.0020 | 0.20 |
| 30 | 158.0 | 0.0020 | 0.20 |
| 29 | 158.0 | 0.0020 | 0.20 |
| 28 | 158.0 | 0.0020 | 0.20 |
| 27 | 158.0 | 0.0020 | 0.20 |
| 26 | 158.0 | 0.0020 | 0.20 |
| 25 | 158.0 | 0.0020 | 0.20 |
| 24 | 158.0 | 0.0020 | 0.20 |
| 23 | 158.0 | 0.0020 | 0.20 |
| 22 | 158.0 | 0.0020 | 0.20 |
| 21 | 158.0 | 0.0020 | 0.20 |
| 20 | 158.0 | 0.0020 | 0.20 |
| 19 | 158.0 | 0.0020 | 0.20 |
| 18 | 158.0 | 0.0020 | 0.20 |
| 17 | 158.0 | 0.0020 | 0.20 |
| 16 | 158.0 | 0.0020 | 0.20 |
| 15 | 158.0 | 0.0020 | 0.20 |
| 14 | 158.0 | 0.0020 | 0.20 |
| 13 | 158.0 | 0.0020 | 0.20 |
| 12 | 158.0 | 0.0020 | 0.20 |
| 11 | 158.0 | 0.0020 | 0.20 |
| 10 | 158.0 | 0.0021 | 0.21 |
| 9 | 158.0 | 0.0021 | 0.21 |
| 8 | 158.0 | 0.0021 | 0.21 |
| 7 | 158.0 | 0.0021 | 0.21 |
| 6 | 158.0 | 0.0021 | 0.21 |
| 5 | 158.0 | 0.0021 | 0.21 |
| 4 | 158.0 | 0.0021 | 0.21 |
| 3 | 158.0 | 0.0021 | 0.21 |
| 2 | 158.0 | 0.0021 | 0.21 |
| 1 | 158.0 | 0.0021 | 0.21 |
| Feed to primary extractor | 7.9 | 0.00 | 0.21 |
| Recycle | 150 | 0.00 | 0.21 |

The invention claimed is:

1. A process for recovering a volatile carboxylic acid from an aqueous stream comprising same, the process comprising the steps of:
   (i) steam stripping the carboxylic acid from the aqueous stream, which aqueous stream is produced by a conversion process using a lignocellulosic feedstock as a substrate, the steam stripping comprising contacting the aqueous stream with steam by flowing the aqueous stream and the steam countercurrent to one another, thereby producing a vapour stream comprising vapourized carboxylic acid and steam and a stripped aqueous stream;
   (ii) extracting the vapourized carboxylic acid with an organic solvent by contacting the vapour stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water;
   (iii) returning the steam from step (ii) to the steam stripping step (step i) to further strip the carboxylic acid from the aqueous stream; and
   (iv) separating the carboxylic acid from the organic solvent.

2. The process of claim 1, wherein the steam stripping is conducted in a stripping column and the extracting is conducted in a separate extracting column.

3. The process of claim 1, wherein the steam stripping and extracting are conducted in a single column comprising alternating and superimposed stripping and extracting stages.

4. The process of claim 1, wherein the carboxylic acid that is extracted is recovered from the organic solvent.

5. The process of claim 1, wherein the carboxylic acid is separated from the organic solvent by distillation.

6. The process of claim 5, wherein organic solvent obtained from the step of separating is reused in the process.

7. The process of claim 1, wherein, in the step of extracting, the organic solvent comprises an aliphatic amine having at least 10 carbon atoms and phenols, naphthols or alkylated phenols having 1 to 40 carbon atoms in their alkyl group.

8. The process of claim 7, wherein the alkylated phenols are nonylphenol or octylphenol.

9. The process of claim 7, wherein the aliphatic amine is selected from the group consisting of tributylamine, tripentylamine, trihexylamine, trioctylamine, tridecylamine and mixtures thereof.

10. The process of claim 1, wherein the stripping is conducted at a temperature of about 40° C. to about 145° C.

11. The process of claim 1, wherein the carboxylic acid that is recovered is acetic acid.

12. The process of claim 1, wherein, in the step of extracting, water is insoluble in the organic solvent.

13. The process of claim 1, wherein the concentration of the carboxylic acid that is present in the aqueous stream fed to the stripping column is at a concentration of less than about 5 wt %.

14. A process for recovering a volatile carboxylic acid from an aqueous stream comprising same, the process comprising the steps of:
(i) steam stripping the carboxylic acid from the aqueous stream, which aqueous stream is produced by a conversion process that comprises the steps of pretreating a lignocellulosic feedstock with acid or alkali to produce a pretreated feedstock composition comprising fiber solids containing cellulose, hydrolyzing the cellulose to glucose with cellulase enzymes and β-glucosidase and fermenting the glucose to ethanol or butanol, the steam stripping comprising contacting the aqueous stream with steam by flowing the aqueous stream and the steam countercurrent to one another, thereby producing a vapour stream comprising vapourized carboxylic acid and steam and a stripped aqueous stream;
(ii) extracting the vapourized carboxylic acid with an organic solvent by contacting the vapour stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water;
(iii) returning the steam from step (ii) to the steam stripping step (step i) to further strip the carboxylic acid from the aqueous stream; and
(iv) separating the carboxylic acid from the organic solvent.

15. A process for recovering a volatile carboxylic acid from an aqueous stream comprising same, the process comprising the steps of:
(i) steam stripping the carboxylic acid from the aqueous stream, which aqueous stream is produced by a conversion process that comprises the steps of pretreating a lignocellulosic feedstock with acid to produce a pretreated feedstock composition comprising fiber solids containing cellulose, hydrolyzing the cellulose to glucose with cellulase enzymes and β-glucosidase and fermenting the glucose to ethanol, the steam stripping comprising contacting the aqueous stream with steam by flowing the aqueous stream and the steam countercurrent to one another, thereby producing a vapour stream comprising vapourized carboxylic acid and steam and a stripped aqueous stream;
(ii) extracting the vapourized carboxylic acid with an organic solvent by contacting the vapour stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water;
(iii) returning the steam from step (ii) to the steam stripping step (step i) to further strip the carboxylic acid from the aqueous stream; and
(iv) separating the carboxylic acid from the organic solvent.

16. A process for recovering a volatile carboxylic acid from an aqueous stream comprising same, the process comprising the steps of:
(i) steam stripping the carboxylic acid from the aqueous stream, which aqueous stream is produced by a conversion process using a lignocellulosic feedstock as a substrate, the steam stripping comprising contacting the aqueous stream with steam by flowing the aqueous stream and the steam countercurrent to one another, thereby producing a vapour stream comprising vapourized carboxylic acid and steam and a stripped aqueous stream;
(ii) extracting the vapourized carboxylic acid with an organic solvent having a distribution coefficient of at least 5 by contacting the vapour stream with the organic solvent to produce (a) a stream comprising the organic solvent and the carboxylic acid and (b) the steam at least substantially depleted of the carboxylic acid, wherein the organic solvent has an atmospheric boiling point of at least about 150° C. and is insoluble in water;
(iii) returning the steam from step (ii) to the steam stripping step (step i) to further strip the carboxylic acid from the aqueous stream; and
(iv) separating the carboxylic acid from the organic solvent.

* * * * *